United States Patent
Haase (10) Patent No.: US 8,323,267 B2
(45) Date of Patent: Dec. 4, 2012

(54) INFUSION DEVICE WITH ACTIVE AND PASSIVE CHECK VALVES

(75) Inventor: James Martin Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1736 days.

(21) Appl. No.: 11/412,464

(22) Filed: Apr. 27, 2006

(65) Prior Publication Data

US 2007/0255261 A1 Nov. 1, 2007

(51) Int. Cl.
*A61K 9/22* (2006.01)
*A61M 5/00* (2006.01)

(52) U.S. Cl. .................. 604/891.1; 604/890.1; 604/247

(58) Field of Classification Search ................. 604/247, 604/502, 890.1, 891.1
See application file for complete search history.

(56) References Cited

U.S. PATENT DOCUMENTS

| | | |
|---|---|---|
| 3,963,380 A | 6/1976 | Thomas, Jr. et al. |
| 4,360,019 A | 11/1982 | Portner et al. |
| 4,692,147 A | 9/1987 | Duggan |
| 4,714,462 A | 12/1987 | DiDomenico |
| 4,772,263 A | 9/1988 | Dorman et al. |
| 5,011,472 A | 4/1991 | Aebischer et al. |
| 5,073,094 A | 12/1991 | Dorman et al. |
| 5,158,547 A | 10/1992 | Doan et al. |
| 5,520,667 A * | 5/1996 | Roche ........................... 604/290 |
| 5,725,017 A | 3/1998 | Elsberry et al. |
| 5,954,058 A | 9/1999 | Flaherty |
| 6,152,898 A | 11/2000 | Olsen |
| 6,228,050 B1 | 5/2001 | Olsen et al. |
| 6,488,652 B1 | 12/2002 | Weijand et al. |
| 6,554,822 B1 | 4/2003 | Holschneider et al. |
| 6,656,158 B2 | 12/2003 | Mahoney et al. |
| 2002/0173773 A1 | 11/2002 | Olsen |
| 2002/0173774 A1 | 11/2002 | Olsen |
| 2003/0130647 A1 | 7/2003 | Gray et al. |
| 2003/0216683 A1 * | 11/2003 | Shekalim ........................ 604/67 |
| 2005/0024175 A1 | 2/2005 | Gray et al. |
| 2005/0187515 A1 * | 8/2005 | Varrichio et al. ............... 604/67 |
| 2007/0016171 A1 * | 1/2007 | Podvin et al. .............. 604/891.1 |

FOREIGN PATENT DOCUMENTS

| | | |
|---|---|---|
| DE | 102 61 610 A1 | 7/2004 |
| EP | 0 142 866 A2 | 5/1985 |
| EP | 0 183 351 A1 | 6/1986 |
| EP | 0 142 866 A3 | 12/1986 |
| EP | 1 058 565 B1 | 5/2003 |
| WO | WO 80/01755 A1 | 9/1980 |
| WO | WO 03/099351 A2 | 12/2003 |

OTHER PUBLICATIONS

U.S. Appl. No. 11/412,375, filed Apr. 27, 2006, Haase.
U.S. Appl. No. 11/412,592, filed Apr. 27, 2006, Haase.
U.S. Appl. No. 11/412,443, filed Apr. 27, 2006, Haase.

(Continued)

*Primary Examiner* — Victoria P Shumate (57) ABSTRACT

An infusion system in which therapeutic substance from a reservoir is pumped by a bolus pump to an infusion port is disclosed. The therapeutic substance delivered by the bolus pump passes first through a passive check valve located downstream from the pump. The passive check valve opens in response to fluid pressure of the therapeutic substance. After passing through the passive check valve, the therapeutic substance passes through an active check valve located downstream from the passive check if the active check valve is actuated such that it is open. When not activated, the active check valve is closed and fluid flow through the active check valve in the downstream direction is prevented.

21 Claims, 3 Drawing Sheets

OTHER PUBLICATIONS

"Programmable Infusion System, The SynchroMed Pump" datasheet [online]. Medtronic, Inc., Minneapolis, MN, [retrieved on May 18, 2006]. Last updated Sep. 5, 2001. Retrieved from the Internet: <URL:http://www.medtronic.com/neuro/paintherapies/pain_treatment_ladder/drug_infusion/pumps_pump_sel/synchromed_pumps.html>; 6 pgs.

"SynchroMed Infusion System: Clinical Reference Guide for Pain Therapy" [online]. Medtronic, Inc., Minneapolis, MN, [retrieved on Oct. 4, 2006]. Retrieved from the Internet: <URL: http://www.medtronic.com/neuro/paintherapies/pain_treatment_ladder/pdf/1_reference_guide.pdf>; 81 pgs.

* cited by examiner

INFUSION DEVICE WITH ACTIVE AND PASSIVE CHECK VALVES

TECHNICAL FIELD

The present invention relates generally to a medical device and, more particularly, to an implantable infusion device including a bolus pump delivering a therapeutic substance through a passive check valve and an active check valve.

BACKGROUND

Treatment of diseases and ailments of the body often benefit from short—or long-term infusion of drugs and/or other fluids. While such therapeutic substances may be administered extracorporally, e.g., via transcutaneous injection, many patient benefit from the consistent and repeatable dosage provided by an implantable infusion pump. Such pumps may be used in a variety of applications such as control of pain and/or spasticity. They are well-suited to deliver infusate fluids to a targeted delivery site such as an epidural or intrathecal space of the spinal canal, or a particular location within the brain.

Implantable infusion pumps are typically implanted subcutaneously, e.g., in the chest or abdominal cavity. The pump may incorporate a reservoir to hold the infusate fluid. A self-sealing, needle-penetrable septum may also be provided and is preferably located generally directly beneath the skin. The septum provides a fluid passageway that permits the reservoir to be refilled periodically via a transcutaneous injection. Accordingly, the pump reservoir can be filled or refilled without requiring surgical removal from the patient's body, and further without requiring any other significant surgical procedure.

The pump may also include a discharge outlet through which the therapeutic substance is directed during delivery. The outlet is typically connected to flexible medical tubing, e.g., a catheter, leading to the targeted delivery site. In addition to the reservoir, infusion pumps may further include a power source, a pump, and associated electronics to control delivery of the therapeutic substance to the patient in accordance with a prescribed schedule.

Active or programmable infusion devices using a pump or similar metering mechanism to deliver the desired drug dosage are commonly used. Active devices typically include a drug reservoir, a pump to transport the drug from the reservoir, and an outlet port coupled to a flexible catheter, the latter operable to carry the drug to the desired location within the body. Such devices may further include a battery to power the pump, as well as associated electronics to control various device parameters, e.g., pump flow rate. Some active devices may further include an antenna that permits remote programming of the device once implanted. An example of an active drug infusion device is the SYNCHROMED line of programmable pumps produced by Medtronic, Inc.

Regardless of what type of infusion device is utilized, a primary goal is to ensure that only a specific volume of the therapeutic substance is delivered to the patient. Yet, various factors may adversely impact precise substance delivery. For example, some medical devices may utilize a flexible reservoir that is exposed to surrounding tissue and thus to ambient pressure, e.g., the reservoir is not protected by a shell of the medical device. With such devices, the application of an external force may compress the reservoir and thus elevate reservoir pressure. The pump, seals, and other components downstream of the reservoir may then be exposed to this elevated pressure, potentially resulting in excess substance infusion and/or component (e.g., pump) damage.

Implantable infusion devices for delivering therapeutic substances to a patient using solenoid piston pumps are described in U.S. Patent Application Publication No. US 2002/0173773 (Olsen). Although these implantable infusion devices offer many advantages in areas such as, e.g., energy efficiency, size, compatibility with therapeutic substances, etc., further improvements in the implantable infusion devices are possible.

For example, further enhancements in, e.g., energy efficiency and/or accuracy may be possible by addressing the arrangement and use of valves to control the output of the pump.

SUMMARY OF THE INVENTION

The present invention provides an infusion system in which therapeutic substance from a reservoir is pumped by a bolus pump to an infusion port. The therapeutic substance delivered by the bolus pump passes first through a passive check valve located downstream from the pump. The passive check valve opens in response to fluid pressure of the therapeutic substance. After passing through the passive check valve, the therapeutic substance passes through an active check valve located downstream from the passive check if the active check valve is actuated such that it is open. When not activated, the active check valve is closed and fluid flow through the active check valve in the downstream direction is prevented.

The use of an active check valve located in the fluid pathway downstream of the pump may enhance energy efficiency in an infusion device by reducing flow resistance for therapeutic substance as compared to infusion devices in which therapeutic substance must be forced through normally closed passive check valves. Flow resistance may preferably be reduced because the active check valve does not rely on fluid pressure exerted on the valve using the pump to open a valve. For example, if the active check valve is in the form of a solenoid check valve, one or more coils may be energized to open the check valve. It may be preferred that the opening occur slightly before or at the same time as a pumping event.

In some embodiments incorporating a normally closed active check valve downstream from a pump as described herein, the likelihood of excess substance infusion due to inadvertent over-pressurization of the device reservoir may be substantially reduced or eliminated. This protection may be afforded without the introduction of potential flow interruptions downstream that would be provided using, e.g., a forward-opening check valve with a high cracking pressure. As a result, the active check valves may prevent flow when needed, yet limit interference with fluid flow during normal device operation. Still further, some active check valves as described herein as "back-closing" may correspondingly increase sealing pressure as reservoir pressure elevates (and/or ambient pressure decreases), improving substance containment even at relatively high differential pressures.

The combination of a passive check valve arranged to allow flow in the downstream direction and prevent flow in the upstream direction provided in series with an active check valve provided downstream of the passive check valve to allow flow in the downstream direction when activated, but prevent flow in the downstream direction when closed may provide an infusion device in which energy efficiency and safety may be improved.

The pumps used in connection with the present invention should be capable of delivering discrete bolus amounts of therapeutic substances at selected intervals to the valve assembly located between the pump and the infusion port. Each bolus delivery will typically be separated from the preceding and succeeding delivery events by a period during which no therapeutic substance is delivered. Such pumps will be described herein as "bolus pumps".

Many different bolus pumps may be used in the infusion devices of the present invention, including, but not limited to, piston pumps, diaphragm pumps, piezoelectric pumps, etc. Examples of some potentially suitable solenoid piston pumps that may be used in connection with the infusion devices of the invention may be described in U.S. Patent Application Publication No. US 2002/0173773 A1 (Olsen), titled PERMANENT MAGNET SOLENOID PUMP FOR AN IMPLANTABLE THERAPEUTIC SUBSTANCE DELIVERY DEVICE.

In one aspect, the present invention provides an implantable therapeutic substance infusion device that includes a therapeutic substance reservoir; control electronics operably connected to a power source; a bolus pump operably connected to the power source and the control electronics, the bolus pump further operably connected to the reservoir and configured to pump a therapeutic substance from the therapeutic substance reservoir in a downstream direction from the bolus pump to an infusion port in response to a pump signal received from the control electronics; a passive check valve located in a fluid pathway between the infusion port and the bolus pump, the passive check valve comprising a normally closed valve that opens in response to fluidic pressure generated by operation of the bolus pump; and an active check valve located in the fluid pathway between the passive check valve and the infusion port, wherein the active check valve comprises a normally closed valve that opens in response to an open signal from the control electronics, and wherein fluid flow in the downstream direction through the active check valve is prevented when the active check valve is closed.

In another aspect, the present invention provides an implantable therapeutic substance infusion device that includes a therapeutic substance reservoir; control electronics operably connected to a power source; a bolus pump operably connected to the power source and the control electronics, the bolus pump further operably connected to the reservoir and configured to pump a therapeutic substance from the therapeutic substance reservoir in a downstream direction from the bolus pump to an infusion port in response to a pump signal received from the control electronics; a passive check valve located in a fluid pathway between the infusion port and the bolus pump, the passive check valve comprising a normally closed valve that opens in response to fluidic pressure generated by operation of the bolus pump; a solenoid check valve located in the fluid pathway between the passive check valve and the infusion port, the solenoid check valve comprising a normally closed valve that opens in response to an open signal from the control electronics, wherein fluid flow in the downstream direction through the solenoid check valve is prevented when the solenoid check valve is closed, and wherein fluid pressure on an upstream side of the solenoid check valve increases the energy required to open the solenoid check valve; and an implantable biocompatible housing, wherein the power source, control electronics, bolus pump, passive check valve, and solenoid check valve are contained within the housing.

In another aspect, the present invention provides an method of operating an implantable therapeutic substance infusion device. The method includes providing an implantable therapeutic substance infusion device that includes a therapeutic substance reservoir; control electronics operably connected to a power source; a bolus pump operably connected to the power source and the control electronics, the bolus pump further operably connected to the therapeutic substance reservoir and configured to pump a therapeutic substance from the therapeutic substance reservoir in a downstream direction from the bolus pump to an infusion port; a passive check valve located in a fluid pathway between the infusion port and the bolus pump, the passive check valve comprising a normally closed valve that opens in response to fluidic pressure generated by operation of the bolus pump; a solenoid check valve located in the fluid pathway between the passive check valve and the infusion port, the solenoid check valve comprising a normally closed valve that opens when actuated by the control electronics, wherein the solenoid check valve includes one or more fluid passages formed therethrough, and wherein fluid flow in the downstream direction through the solenoid check valve is prevented when the solenoid check valve is closed, and further wherein fluid pressure on an upstream side of the solenoid check valve increases the energy required to open the solenoid check valve; and an implantable biocompatible housing, wherein the power source, control electronics, bolus pump, passive check valve, and solenoid check valve are contained within the housing. The method further includes actuating the bolus pump to move a bolus of therapeutic substance in the downstream direction, whereby the passive check valve opens in response to pressure exerted on an upstream side of the passive check valve by the bolus of therapeutic substance; and opening the solenoid check valve by energizing a coil, whereby the bolus of therapeutic substance passes through the one or more fluid passages in the solenoid check valve towards the infusion port.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention is directed to medical devices and, in particular, to infusion devices and systems that are implanted within a patient's body. Infusion devices in accordance with embodiments of the present invention typically incorporate a pair of check valves including a normally closed passive check valve and an active check valve provided in series downstream from a pump mechanism.

A "passive check valve" as used in connection with the present invention refers to a normally closed check valve that moves from its normally closed state to an open state in response to fluid pressure exerted on the upstream side of the valve and, further, a valve in which flow in the upstream direction through the valve is blocked. The valve may also be described as "forward-opening" to indicate that pressure on the upstream side can force the valve open, thus allowing fluid flow in the downstream (or forward) direction.

An "active check valve" as used in connection with the present invention refers to a normally closed check valve that includes a mechanism to move the valve from its normally closed state to an open state. Flow in the downstream direction through the active check valve is blocked when the valve is closed. In some embodiments, the active check valves may be constructed and arranged such that fluid pressure on the upstream side of the valve acts to force the valve closed, further assisting in the prevention of downstream fluid flow through the valve when not actively opened (such check valves may be described as "back-closing" check valves).

Examples of some potentially suitable mechanisms used to move the active check valves from their normally closed state to an open state where fluid can pass the valves may include, e.g., solenoids, rotary devices, etc. For example, check valves using solenoid mechanisms may typically include one or more coils, magnets or magnetizable material, and one or more biasing elements used to keep the valve in its normally closed state when the one or more coils are not energized. Active check valves that use solenoid mechanisms to move from a normally closed to open state may be referred to herein as "solenoid check valves". Rotary mechanisms (e.g., stepper motors, etc.) may be used to rotate components to move the valve from its normally closed state to an open state.

With either the passive or active check valves used in connection with the present invention, although flow in one direction through the valve is described as prevented, it should be understood that some minimal amount of fluid may pass through the valve if, e.g., the pressure exerted by the fluid exceeds the sealing capabilities of the valve mechanisms.

It is noted that the terms "comprises" and variations thereof do not have a limiting meaning where these terms appear in the accompanying description and claims. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

Figure 1:
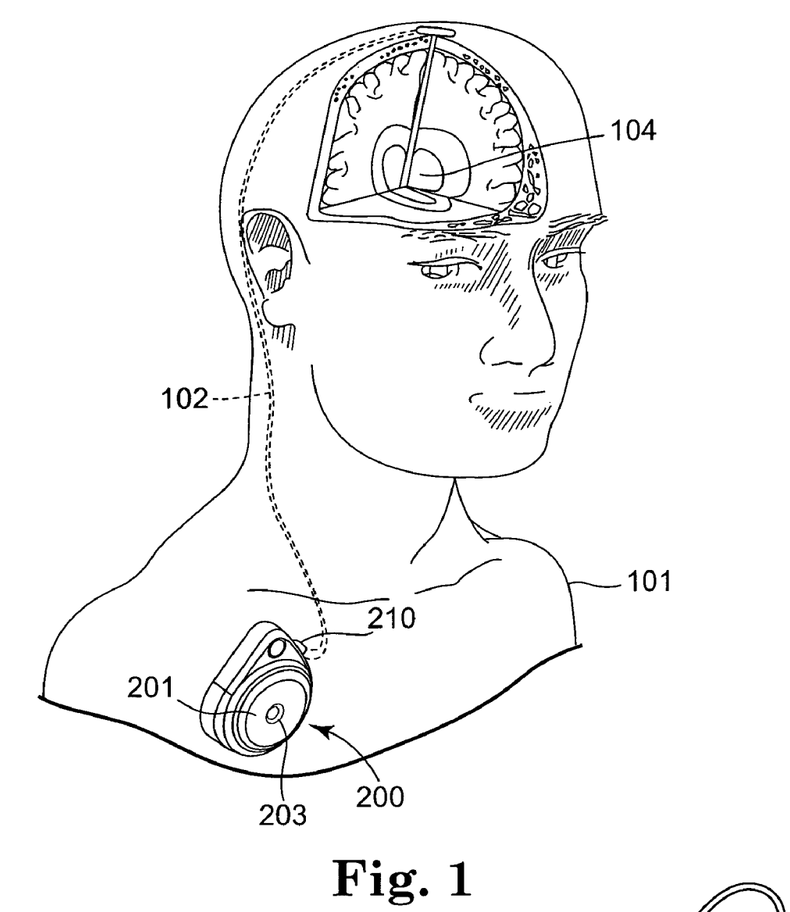
FIG. 1 illustrates an exemplary medical system, e.g., implantable infusion system, as it may be implanted in a patient's body, wherein the system incorporates an active infusion device in accordance with one embodiment of the present invention.
Figure 2:
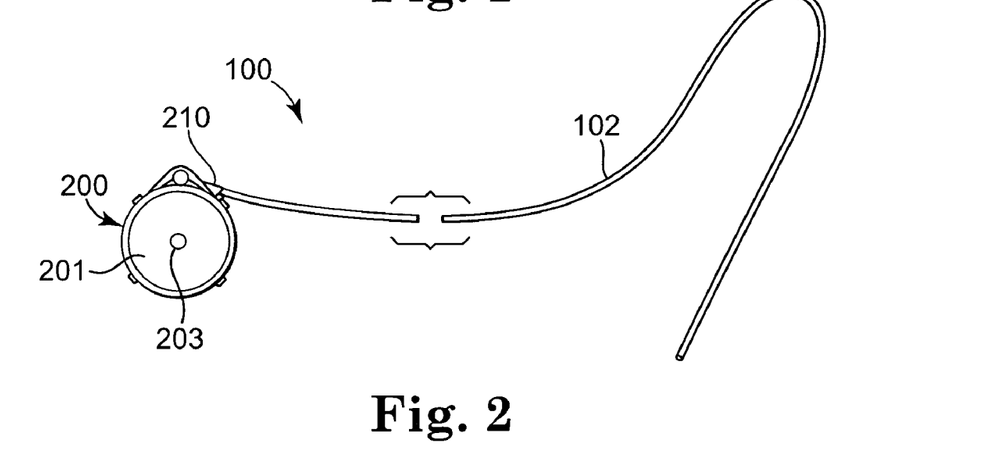
FIG. 2 is a view of the infusion system of FIG. 1 removed from the body.

FIGS. 1 and 2 illustrate an implantable medical system, such as a therapeutic substance infusion system, in accordance with one embodiment of the invention (FIG. 1 illustrates one system as it may be implanted within the patient's body 101, while FIG. 2 illustrates the system isolated, i.e., outside the body). The exemplary infusion system includes a medical device, e.g., implantable medical device 200, and preferably at least one catheter 102. Such infusion systems may be used for a wide variety of therapies including treatment of pain, spasticity, and other medical conditions.

The device 200 and catheter 102 are typically implanted by a clinician (e.g., surgeon) within the body 101 during a surgical procedure. While the present invention also contemplates embodiments wherein the catheter is implanted with one end outside the body so that it may attach to an external infusion device, the remainder of this description is, for the sake of brevity, directed to implantable medical systems.

Before implantation of the infusion device 200, the catheter 102 may be positioned with its distal end (i.e., the end that does not couple to the device) located at a desired therapy delivery site 104 within the body 101, e.g., within the brain (while shown as delivering a therapeutic substance to a site 104 within the brain, the distal end of the catheter 102 may be located at most any location within the body 101, e.g., an epidural or intrathecal space of the spinal canal). A proximal end of the catheter 102 may be tunneled through the tissue to the device implant location and coupled to an infusion port 210 of the device 200. If implanted the infusion device 200 is typically implanted subcutaneously, e.g., about 2.5 cm (1 inch) beneath the skin, where there is sufficient tissue for supporting the device, e.g., with sutures or the like.

The device 200 is, in the illustrated embodiment, operable to infuse a therapeutic substance (also referred to as "drug" herein) from an enclosed substance or drug reservoir into the body 101. The "therapeutic substance" may be a substance intended to have a therapeutic effect on the patient, e.g., pharmaceutical compositions, genetic materials, biologics, and other substances.

"Pharmaceutical compositions," as used herein, may include chemical formulations intended to have a therapeutic effect such as intrathecal antispasmodics, pain medications, chemotherapeutic agents, and the like. Pharmaceutical compositions are often configured to function effectively in an implanted environment by possessing various characteristics including: stability at body temperature to retain therapeutic qualities; concentration to reduce the frequency of replenishment; and the like. "Genetic materials," as used herein, may include substances intended to have a direct or indirect genetic therapeutic effect such as genetic vectors, genetic regulator elements, genetic structural elements, DNA, and the like. "Biologics," as used herein, may include substances that are living matter, or derived from living matter, and offer a therapeutic effect to the patient such as stem cells, platelets, hormones, biologically produced chemicals, and the like. "Other substances" may include most any other substance that is intended to have a therapeutic effect, yet does not clearly fit within one of the categories identified above. Examples of other substances may include saline solutions, fluoroscopy agents, and the like.

In some embodiments, the therapeutic substance contained within a reservoir of the infusion device 200 may be replenished periodically after device implantation. Typically, replenishment is accomplished with a non-coring needle (not shown) connected to a syringe filled with the therapeutic substance. The needle may be inserted through the patient's skin and into a self-sealing septum 203 located within the housing 201 of the device 200.

Figure 3:
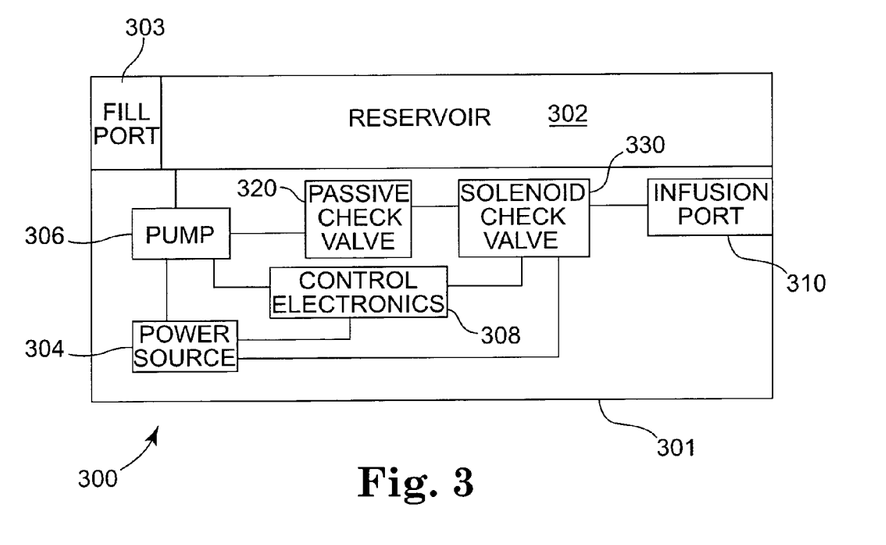
FIG. 3 is a schematic diagram of one exemplary infusion device including a bolus pump feeding therapeutic substance to a passive check valve and an active check valve mounted in series between the pump and an infusion port.

FIG. 3 is a schematic diagram depicting components that may be included in one exemplary embodiment of the infusion device 300. As shown in the diagram, the infusion device 300 may include a housing 301 that encloses various components in the device 300. One depicted component is a reservoir 302 for containing a therapeutic substance to be delivered to a patient by the infusion device 300. Other components that may be provided as a part of the infusion device 300 include a power source 304, bolus pump 306, control electronics 308, infusion port 310, passive check valve 320, and active check valve 330. Other components not specifically depicted in FIG. 3 may also be included in the housing 301, e.g., valves to control fluid flow, overfill protection devices, etc.

The housing 301 of the infusion device 300 may be in the form of a single housing manufactured from a biocompatible material such as titanium, tantalum, stainless steel, plastic, ceramic, and/or the like. However, one or more components of the infusion device may also be located in separate housings that are appropriately coupled to each other. For example, the reservoir 302 could be attached to or placed within the housing 301, or it could be separated from the housing 301 and provided within its own housing that is connected to housing 301 via, e.g., a fluid coupling.

The power source 304 may preferably be an electric power source in the form of, e.g., a battery, capacitor, etc. The power source 304 may preferably be operatively connected to supply power to the bolus pump 306, control electronics 308 and active check valve 330.

The control electronics 308 may preferably include memory and a controller. The controller may be an Application Specific Integrated Circuit (ASIC) state machine, a gate array, and/or may include a microprocessor. The control electronics 308 are preferably configured to operate the pump 306 (e.g., controlling infusion rate, etc.). The control electronics 308 may also include components, etc. to operate other features such as valves, sensors (temperature, density, etc.), patient alarms, etc. The control electronics 308 may further include telemetry components configured to receive and/or send information after the infusion device 300 is implanted in a patient. Telemetry may be used to, e.g., allow programming of the infusion rate, infusion times, etc. Telemetry may also be used to provide information from the infusion device such as, e.g., the amount of therapeutic substance in the reservoir, etc. Such information may be used to determine whether the reservoir requires refilling, etc.

Also depicted in FIG. 3 is a fill port 303 located in the housing 301. The fill port 303 may take the form of, e.g., a septum, etc., capable of receiving a device to fill the reservoir 302 with a therapeutic substance. Although described as a fill port, it should be understood that the fill port 302 may alternatively be used to remove fluids such as therapeutic substances, air, etc. from the reservoir in addition to or in place of delivering fluid into the reservoir 302. Various systems for refilling reservoirs are known and are not further discussed herein (see, for example, U.S. Pat. Nos. 5,158,547 to Doan et al. and 6,152,898 to Olsen).

The reservoir 302 is also preferably in fluid communication with the inlet side of the pump 306. As a result, therapeutic substance in the reservoir 302 can be supplied to the pump 306 for infusion into a patient as discussed herein. Although not depicted, one or more valves may be used to control delivery fluid from the reservoir 302 to the pump 306.

The reservoir 302 may take any suitable form such as, e.g., a variable volume reservoir formed by an expandable member. An outer surface of the expandable member of the reservoir 302 may be exposed to ambient body pressure such that the pressure of the therapeutic substance within the reservoir 302 can change in response to changes in ambient pressure surrounding the infusion device 300. Other embodiments are also possible in which the reservoir 302 is partially or fully contained within the housing 301 such that the pressure of the therapeutic substance within the reservoir 302 is isolated from ambient pressure.

The pump 306 is preferably operably connected to both the power source 304 and the control electronics 308. As a result, the pump 306 may be powered to transfer therapeutic substance from the reservoir 302 outwardly to the body (through the infusion port 310). As discussed herein, the pump 306 is preferably capable of pumping the therapeutic substance in the downstream direction towards the infusion port 310 in discrete bolus amounts. As each bolus of the therapeutic substance is pumped, the passive check valve 320 preferably opens in response to the fluid pressure exerted on the upstream side of the passive check valve 320 by the therapeutic substance.

The passive check valve 320 is preferably normally closed and forward opening such that fluid pumped in the downstream direction through the infusion device 300 opens the passive check valve 320 when the cracking pressure of the passive check valve 320 is exceeded (where the downstream direction is from the reservoir 302, through pump 306 and towards the infusion port 310). It may also be preferred that the passive check valve 320 prevent fluid flow in the upstream direction (which is opposite the downstream direction).

Because the passive check valve 320 is provided in combination with the active check valve 330, the cracking pressure of the passive check valve 320 (i.e., the pressure at which the valve moves from the closed to open state) may be reduced as compared to systems that rely on passive check valves for all fluid control within an implantable infusion system. The cracking pressure of the passive check valve 320 may be reduced because the active check valve 330 preferably provides the primary control over unwanted fluid delivery in the system. The cracking pressure of the passive check valve 320 may, for example, preferably be two times or less than the differential pressure between the reservoir pressure (i.e., the fluid pressure of the therapeutic substance contained in the reservoir 302) and the expected ambient pressure. For example, if the reservoir pressure is 5 pounds per square inch (psi) (about 35 kPa) above the ambient pressure, the passive check valve may preferably be designed to crack (open) at 10 psi (about 70 kPa) or less. In other instances, the pump 306 may provide sufficient isolation between the passive check valve 320 and the reservoir 302 such that the cracking pressure of the passive check valve 320 may be at or even slightly below the differential pressure between the reservoir pressure and the expected ambient pressure.

The passive check valves used in connection with the present invention may take any suitable construction. Examples of some potentially suitable passive check valve constructions may include, e.g., ball valves, flapper valves, annular flapper valves, reed valves, duckbill valves, poppet valves, etc. Some specific passive check valve constructions that may potentially be used in connection with the present invention are described in U.S. Patent Application Publication No. US 2002/0173774, titled LOW PROFILE INLET VALVE FOR A PISTON PUMP THERAPEUTIC SUBSTANCE DELIVERY DEVICE, filed Sep. 14, 2001.

Furthermore, although the passive check valve 320 is depicted as separate from the pump 306, it should be understood that the passive check valve 320 could be integrated into the pump mechanism 306 itself. Some suitable constructions that incorporate a passive check valve and pump in the same assembly may be found in, e.g., U.S. Patent Application Publication No. U.S. 2002/0173773 A1 (Olsen), titled PERMA- NENT MAGNET SOLENOID PUMP FOR AN IMPLANTABLE THERAPEUTIC SUBSTANCE DELIVERY DEVICE.

The therapeutic substance passing through the passive check valve 320 in the downstream direction must also pass through the active check valve 330 before reaching the infusion port 310. During proper operation of the infusion device 300, the mechanism of the active check valve 330 is activated to open the valve 330, thus allowing the therapeutic substance that has passed through the passive check valve 320 to pass downstream through the active check valve 330. If the active check valve 330 is not actively opened, then the therapeutic substance is prevented from moving downstream past the active check valve 330 because the active check valve 330 is normally closed.

The mechanisms used to move the active check valves between the closed and open states may take a variety of different forms including, but not limited to rotary devices, solenoids, etc. Rotary mechanisms (e.g., stepper motors, etc.) may be used to rotate components to move the valve from its normally closed state to an open state. Solenoid mechanisms used in active check valves of the present invention may typically include one or more coils along with magnets or magnetizable material. The active check valves may also preferably include a biasing element (e.g., a spring, elastomeric member, magnet, etc.) to retain the valve in its normally closed state when the solenoid coil or coils used to open the active check valve are not energized.

Figure 4:
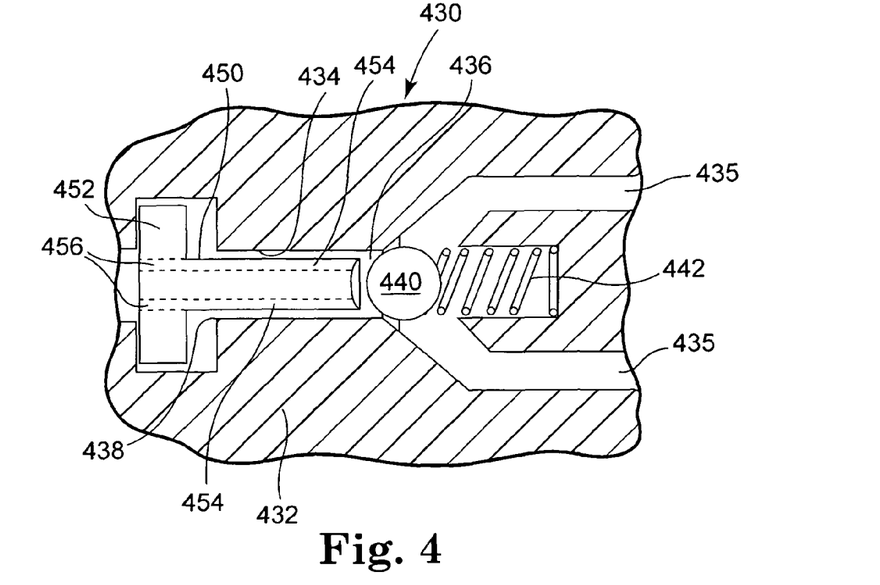
FIG. 4 is a cross-sectional view of one exemplary active check valve in the form of a solenoid check valve, wherein the valve is closed.
Figure 5:
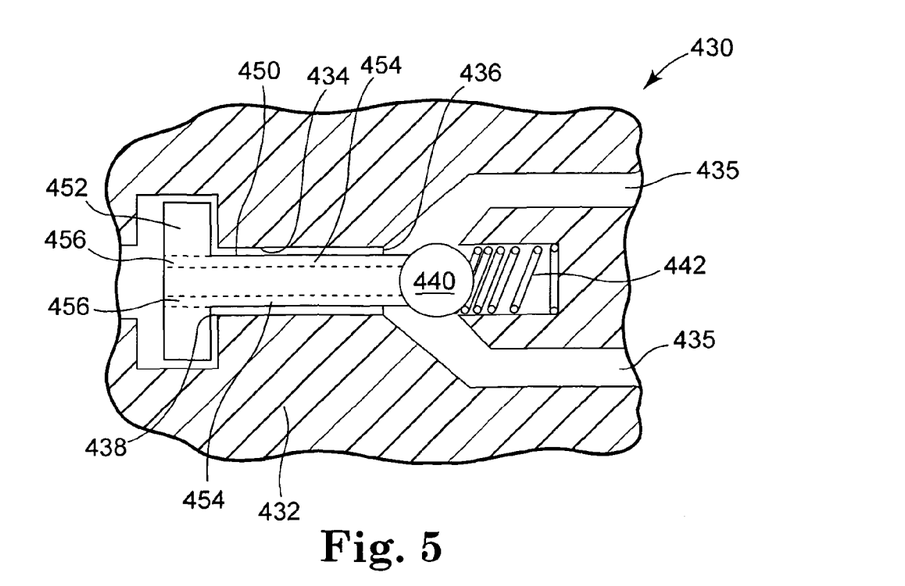
FIG. 5 is a cross-sectional view of the valve of FIG. 4 in which the valve is open.

One example of a potentially suitable design for an active check valve 430 using a solenoid mechanism is depicted in FIGS. 4 & 5. The solenoid check valve 430 includes a housing 432 in which a passageway 434 is located. The passageway 434 opens at an inlet 436 on the upstream side of the valve 430 and an outlet 438 on the downstream side of the valve 430. The housing 432 includes supply passageways 435 through which fluids flow to reach the inlet 436.

The inlet 436 is normally closed in the depicted embodiment by a sealing element 440 which, in the depicted valve 430, is in the form of a ball. The sealing element 440 is biased or pressed against the inlet 436 by a biasing member 442 which, in the depicted embodiment, takes the form of a coil spring although many other structures could be used to close the inlet end of the active check valve 430. It may be preferred that the surfaces around the inlet 436 be shaped to accept the sealing element 440 in a manner that facilitates closure of the valve 430 when the sealing element 440 is seated against the inlet 436.

The valve 430 also includes an actuator 450 positioned within passageway 434. The actuator 450 is used to open the valve 430 to allow fluid to move through passageway 434 in the downstream direction from the inlet 436 to the outlet 438. The actuator 450 opens the valve 430 by moving the sealing element 440 away from the inlet 436, thus allowing fluid to enter the passageway 434 through inlet 436.

FIG. 5 depicts the valve 430 in the open configuration in which the sealing element 440 is forced away from the inlet 436 by the actuator 450 (against the force exerted on the sealing element 440 by the biasing member 442). The outlet end 452 of the actuator 450 may be designed to limit the travel of the actuator 450 in the direction of the sealing element 440. In addition, the housing 432 may be designed to hold the actuator 450 in position within the passageway 434.

Because the depicted actuator 450 is located within the passageway 434 through which fluid flows when the valve 430 is open, the actuator 450 itself may include channels 454 (depicted partially in broken lines in FIG. 5) through which fluid can flow. In addition, the outlet end 452 of the actuator 450 may include one or more bores 456 to facilitate fluid flow through the valve 430.

In the embodiment of the active check valve depicted in FIGS. 4 & 5, the solenoid mechanism may include one or more magnetic components (including, e.g., permanently magnetic material, magnetically susceptible material, magnetizable material, etc.) and one or more coils that can be energized to cause the valve to move between the closed and open states. It may be preferred that the magnetic material be incorporated into the actuator 450 and the coil or coils wound around the passageway 434, such that energizing the coil or coils creates a magnetic field that drives the actuator 450 in the desired direction.

In many respects, solenoid mechanisms used in active check valves of the present invention may be designed based on the principles described in, e.g., U.S. Patent Application Publication No. 2003/0130647 A1 (Gray et al.), titled INFUSION DEVICE AND DRIVING MECHANISM FOR SAME; U.S. Patent Application Publication No. 2005/0024175 A1 (Gray et al.), titled INFUSION DEVICE AND DRIVING MECHANISM AND PROCESS FOR SAME WITH ACTUATOR FOR MULTIPLE INFUSION USES; and U.S. Patent Application Publication No. U.S. 2002/0173773 A1 (Olsen), titled PERMANENT MAGNET SOLENOID PUMP FOR AN IMPLANTABLE THERAPEUTIC SUBSTANCE DELIVERY DEVICE.

Referring again to FIG. 3, it may be preferred that the active check valve 330 in the infusion device 300 be operated such that the solenoid valve 330 opens before the passive check valve 320 opens to release a bolus of the therapeutic substance in the downstream direction (toward the active check valve 330).

By opening the active check valve 330 before delivering a bolus of the therapeutic substance to the upstream side of the active check valve 330, the flow resistance through the infusion device 300 may be reduced. That reduced flow resistance may potentially improve energy efficiency of the infusion device 300. It may further be preferred that the active check valve 330 be operated such that the valve 330 remains open until the bolus of therapeutic substance has passed through the active check valve 330, after which the active check valve 330 can be allowed to return to its normally closed state.

Another potential advantage of opening the active check valve 330 before passing a bolus of therapeutic substance through the passive check valve 320 is that after or during passing of the bolus, pressure on the upstream side of the active check valve typically increases, thus potentially increasing the amount of energy required to open the active check valve 330. Opening the valve 330 before the pressure increase can reduce the energy required to operate the infusion device 300.

By cycling the bolus pump 306 at a programmed frequency in combination with the opening and closing the active check valve 330 based on that programmed frequency, controlled infusion of therapeutic substance using the infusion system 300 may be achieved. As those of skill in the art may appreciate, various parameters, e.g., passive check valve cracking pressures, fluid passageway geometries, and the like, may be selected to reduce flow inefficiencies.

One potential problem with some infusion devices, however, is that the reservoir pressure (i.e., the fluid pressure of the therapeutic substance within the reservoir) may rise above the pressure at which the passive check valve, pump, and other components located between the passive check valve and the reservoir can retain the fluid within the reservoir. Such elevated pressure may potentially resulting in excess substance infusion.

In propellant-based infusion devices (those having reservoirs enclosed within the device housing and pressurized by a propellant contained therein), reservoir pressure may be elevated due to, e.g., increased body temperature or decreased surrounding pressure (the latter, for example, resulting from patient movement to an elevated altitude). Either situation may result in a higher differential pressure inside the reservoir (relative to ambient pressure). In systems that use a flexible reservoir exposed to surrounding tissue and thus to ambient pressure, e.g., the reservoir is not protected by a shell of the medical device. With such devices, the application of an external force may compress the reservoir and thus elevate reservoir pressure.

In a system without an active check valve such as, e.g., active check valve 330, the elevated reservoir pressure may have unintended consequences including, for example, pump damage, seal blow-by, and ultimately, leaking of the therapeutic substance past the pump and passive check valve, potentially resulting in excess substance infusion.

By incorporating an active check valve 330 in accordance with embodiments of the present invention, however, unintended release of the therapeutic substance due to elevated pressure differential between the reservoir 302 and surrounding body (ambient) pressure may be substantially reduced or eliminated. This additional control is provided because, when the active check valve 330 is closed, fluid flow in the downstream direction through the valve 330 is prevented. In some instances, the active check valve 330 may preferably remain closed at fluid pressures up to, e.g., 50 psig (about 350 kPa).

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. An implantable therapeutic substance infusion device comprising:
   a therapeutic substance reservoir;
   control electronics operably connected to a power source;
   a bolus pump operably connected to the power source and the control electronics, the bolus pump further operably connected to the reservoir and configured to pump a therapeutic substance from the therapeutic substance reservoir in a downstream direction from the bolus pump to an infusion port in response to a pump signal received from the control electronics;
   a passive check valve located in a fluid pathway between the infusion port and the bolus pump, the passive check valve comprising a normally closed valve that opens in response to fluidic pressure generated by operation of the bolus pump; and
   an active check valve located in the fluid pathway between the passive check valve and the infusion port, wherein the active check valve comprises a normally closed valve that opens in response to an open signal from the control electronics, wherein fluid pressure on an upstream side of the active check valve increases the energy required to open the active check valve, and wherein fluid flow in the downstream direction through the active check valve is prevented when the active check valve is closed.

2. A device according to claim 1, wherein the fluid pathway comprises an upstream direction from the infusion port to the bolus pump, and wherein the passive check valve closes in response to fluid flow in the upstream direction.

3. A device according to claim 1, wherein the active check valve comprises a solenoid check valve.

4. A device according to claim 3, wherein the solenoid check valve comprises one or more fluid passages formed therethrough.

5. A device according to claim 4, wherein the one or more fluid passages comprises a bore formed through at least a portion of an actuator of the solenoid check valve.

6. A device according to claim 1, wherein the passive check valve comprises a cracking pressure higher than a reservoir pressure of the therapeutic substance in the reservoir.

7. A device according to claim 1, wherein the passive check valve is integral with the bolus pump.

8. A device according to claim 1, wherein the bolus pump comprises a solenoid-activated piston pump.

9. A device according to claim 1, further comprising an implantable biocompatible housing, wherein the power source, control electronics, bolus pump, passive check valve, and active check valve are contained within the housing.

10. An implantable therapeutic substance infusion device comprising:
    a therapeutic substance reservoir;
    control electronics operably connected to a power source;
    a bolus pump operably connected to the power source and the control electronics, the bolus pump further operably connected to the reservoir and configured to pump a therapeutic substance from the therapeutic substance reservoir in a downstream direction from the bolus pump to an infusion port in response to a pump signal received from the control electronics;
    a passive check valve located in a fluid pathway between the infusion port and the bolus pump, the passive check valve comprising a normally closed valve that opens in response to fluidic pressure generated by operation of the bolus pump;
    a solenoid check valve located in the fluid pathway between the passive check valve and the infusion port, the solenoid check valve comprising a normally closed valve that opens in response to an open signal from the control electronics, wherein fluid flow in the downstream direction through the solenoid check valve is prevented when the solenoid check valve is closed, and wherein fluid pressure on an upstream side of the solenoid check valve increases the energy required to open the solenoid check valve; and
    an implantable biocompatible housing, wherein the power source, control electronics, bolus pump, passive check valve, and solenoid check valve are contained within the housing.

11. An implantable therapeutic substance infusion device comprising:
    a therapeutic substance reservoir;
    control electronics operably connected to a power source;
    a bolus pump operably connected to the power source and the control electronics, the bolus pump further operably connected to the reservoir and configured to pump a therapeutic substance from the therapeutic substance reservoir in a downstream direction from the bolus pump to an infusion port in response to a pump signal received from the control electronics;

a passive check valve located in a fluid pathway between the infusion port and the bolus pump, the passive check valve comprising a normally closed valve that opens in response to fluidic pressure generated by operation of the bolus pump, wherein the fluid pathway comprises an upstream direction from the infusion port to the bolus pump, and wherein the passive check valve closes in response to fluid flow in the upstream direction; and an active check valve located in the fluid pathway between the passive check valve and the infusion port, wherein the active check valve comprises a normally closed valve that opens in response to an open signal from the control electronics, wherein fluid flow in the downstream direction through the active check valve is prevented when the active check valve is closed, and wherein fluid pressure on an upstream side of the active check valve increases the energy required to open the active check valve.

12. A device according to claim 11, wherein the active check valve comprises a solenoid check valve comprising one or more fluid passages formed through at least a portion of an actuator of the solenoid check valve.

13. A device according to claim 11, wherein the passive check valve comprises a cracking pressure higher than a reservoir pressure of the therapeutic substance in the reservoir.

14. A device according to claim 11, wherein the passive check valve is integral with the bolus pump.

15. A device according to claim 11, wherein the bolus pump comprises a solenoid-activated piston pump.

16. A device according to claim 11, the device further comprising an implantable biocompatible housing, wherein the power source, control electronics, bolus pump, passive check valve, and active check valve are contained within the housing.

17. An implantable therapeutic substance infusion device comprising:

a therapeutic substance reservoir;

control electronics operably connected to a power source;

a bolus pump operably connected to the power source and the control electronics, the bolus pump further operably connected to the reservoir and configured to pump a therapeutic substance from the therapeutic substance reservoir in a downstream direction from the bolus pump to an infusion port in response to a pump signal received from the control electronics;

a passive check valve located in a fluid pathway between the infusion port and the bolus pump, the passive check valve comprising a normally closed valve that opens in response to fluidic pressure generated by operation of the bolus pump, wherein the fluid pathway comprises an upstream direction from the infusion port to the bolus pump, wherein the passive check valve closes in response to fluid flow in the upstream direction, and wherein the passive check valve comprises a cracking pressure higher than a reservoir pressure of the therapeutic substance in the reservoir; and an active check valve located in the fluid pathway between the passive check valve and the infusion port, wherein the active check valve comprises a normally closed valve that opens in response to an open signal from the control electronics, wherein fluid pressure on an upstream side of the active check valve increases the energy required to open the active check valve, and wherein fluid flow in the downstream direction through the active check valve is prevented when the active check valve is closed.

18. A device according to claim 17, wherein the active check valve comprises a solenoid check valve comprising one or more fluid passages formed through at least a portion of an actuator of the solenoid check valve.

19. A device according to claim 17, wherein the passive check valve is integral with the bolus pump.

20. A device according to claim 17, wherein the bolus pump comprises a solenoid-activated piston pump.

21. A device according to claim 17, the device further comprising an implantable biocompatible housing, wherein the power source, control electronics, bolus pump, passive check valve, and active check valve are contained within the housing.

* * * * *